(12) United States Patent
Yuan et al.

(10) Patent No.: US 10,502,717 B2
(45) Date of Patent: Dec. 10, 2019

(54) METHOD AND SYSTEM FOR MEASURING A WIDEBAND LOOP SENSITIVITY FOR AN ACOUSTIC TRANSDUCER

(71) Applicant: BROADSOUND CORPORATION, Jhubei, Hsinchu County (TW)

(72) Inventors: Ying-Wei Yuan, Jhubei (TW); Jen-Chih Yao, Qionglin Township, Hsinchu County (TW); Fu-Chieh Yang, Hsinchu (TW); Wen-Pin Lai, Hsinchu (TW)

(73) Assignee: BROADSOUND CORPORATION, Hsinchu County (TW)

( * ) Notice: Subject to any disclaimer, the term of this patent is extended or adjusted under 35 U.S.C. 154(b) by 0 days.

(21) Appl. No.: 15/855,677

(22) Filed: Dec. 27, 2017

(65) Prior Publication Data

US 2019/0195835 A1  Jun. 27, 2019

(51) Int. Cl.
*G01N 29/30* (2006.01)
*G01N 29/46* (2006.01)
*G01N 29/34* (2006.01)

(52) U.S. Cl.
CPC .......... *G01N 29/30* (2013.01); *G01N 29/343* (2013.01); *G01N 29/46* (2013.01)

(58) Field of Classification Search
CPC ...... G01N 29/30; G01N 29/46; G01N 29/343; G01N 29/4409; G01N 2291/105; G01H 3/005
USPC .................. 73/1.82, 1.83, 1.86, 1.16; 367/13
See application file for complete search history.

(56) References Cited

PUBLICATIONS

Gomez et al., "Ferroelectret Transducers for Water Immersion and Medical Imaging", 2016, IEEE International Ultrasonics Symposium Proceedings, 4pp.

*Primary Examiner* — Robert R Raevis
(74) *Attorney, Agent, or Firm* — Hauptman Ham, LLP

(57) ABSTRACT

A method and system is disclosed for measuring a wideband loop sensitivity $S_L(f)$ for an acoustic transducer in an acoustic probe. A pulse signal is employed as a wideband reference signal $V_r(t)$; and, in a pulse-echo measurement a corresponding wideband echo signal $V_e(t)$ is obtained. A normalized loop frequency response $\hat{X}(f)$ for the acoustic transducer is defined as a ratio of a Fourier Transform of the $V_e(t)$ to a Fourier Transform of the $V_r(t)$. A wideband loop sensitivity $S_L(f)$ for the acoustic transducer is defined as an absolute square of the $\hat{X}(f)$ in decibel.

18 Claims, 17 Drawing Sheets

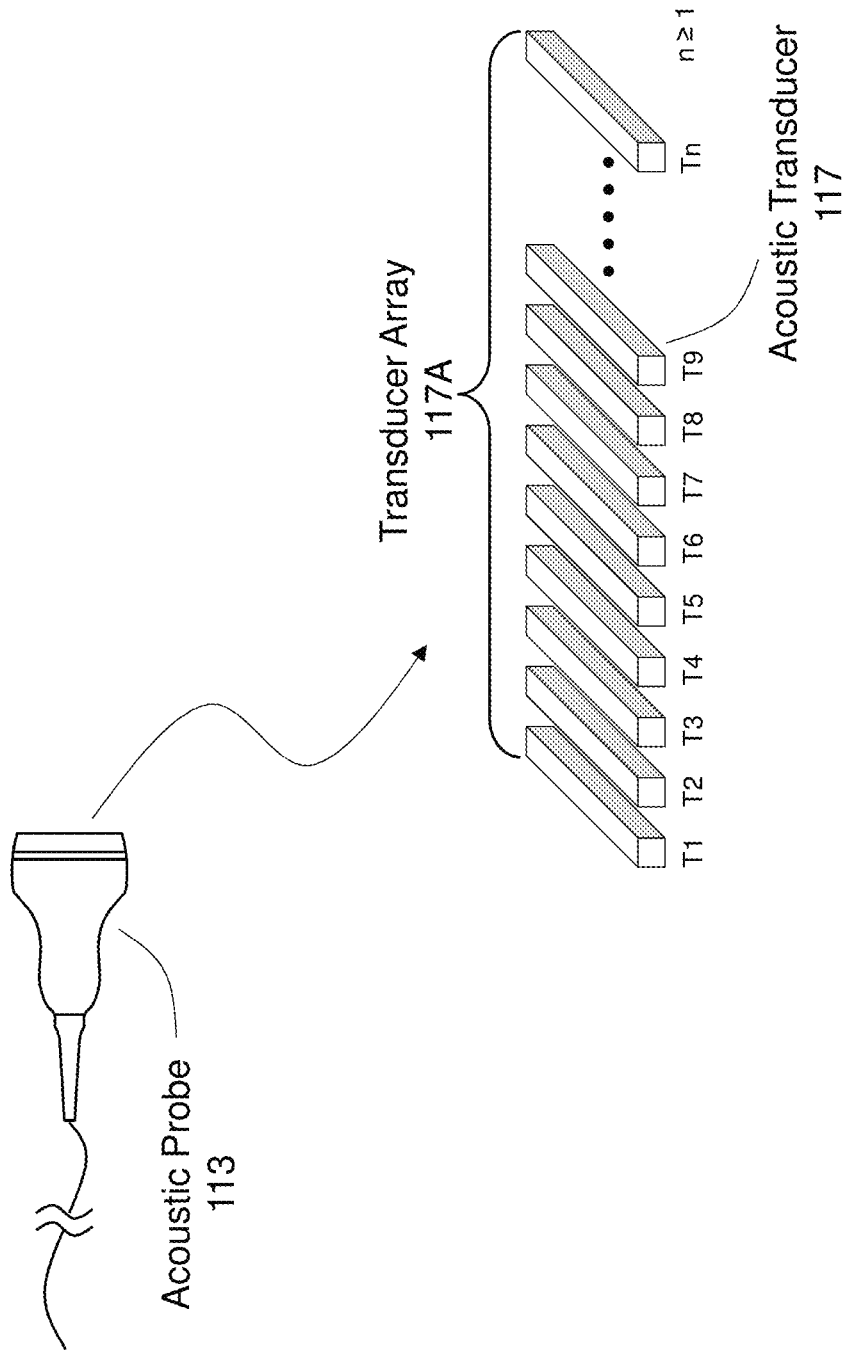

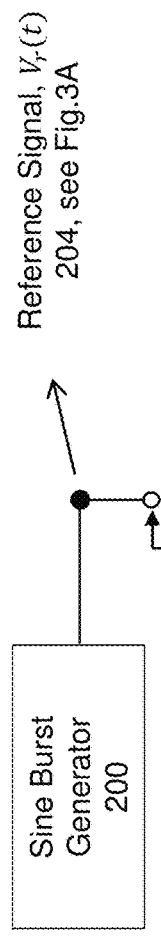
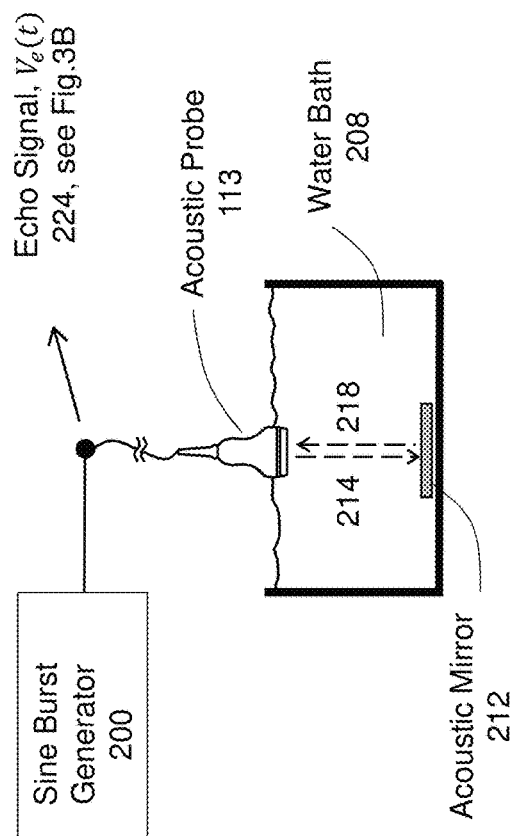

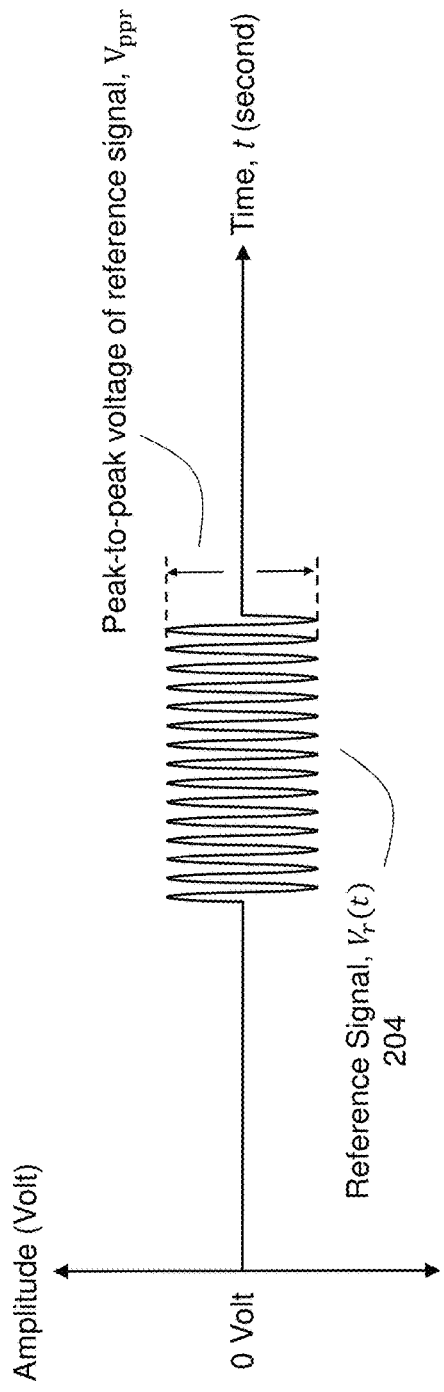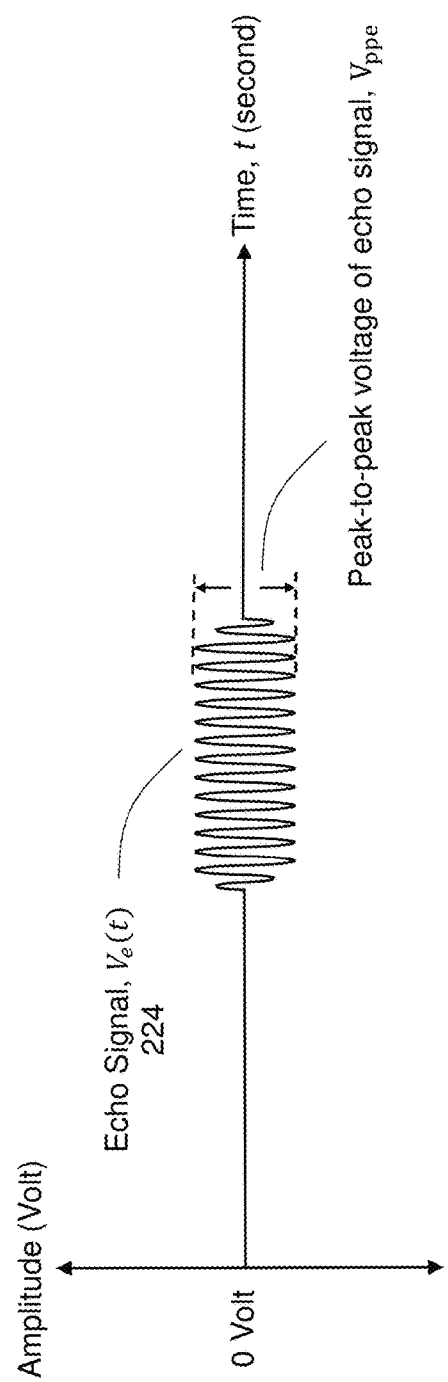

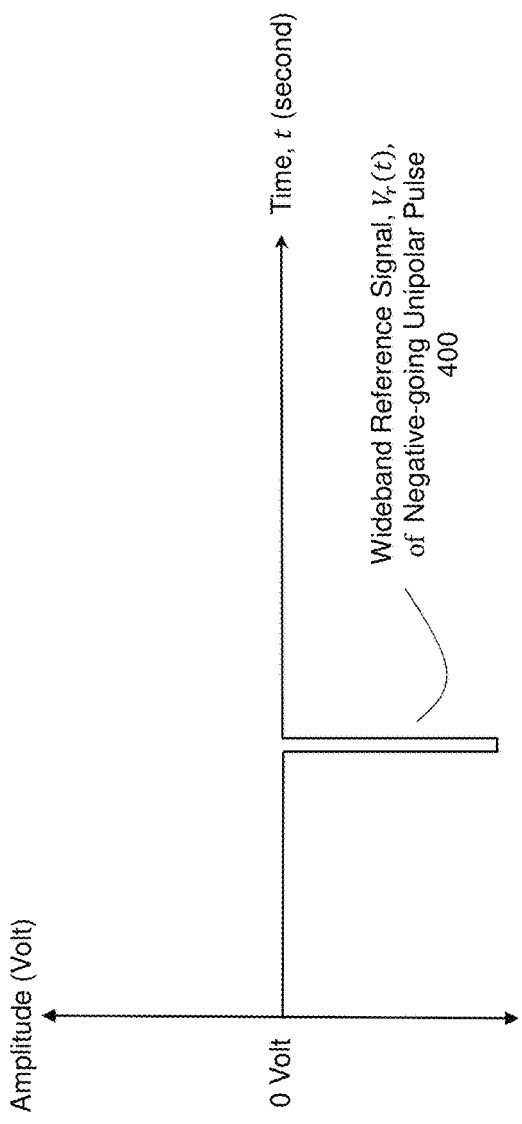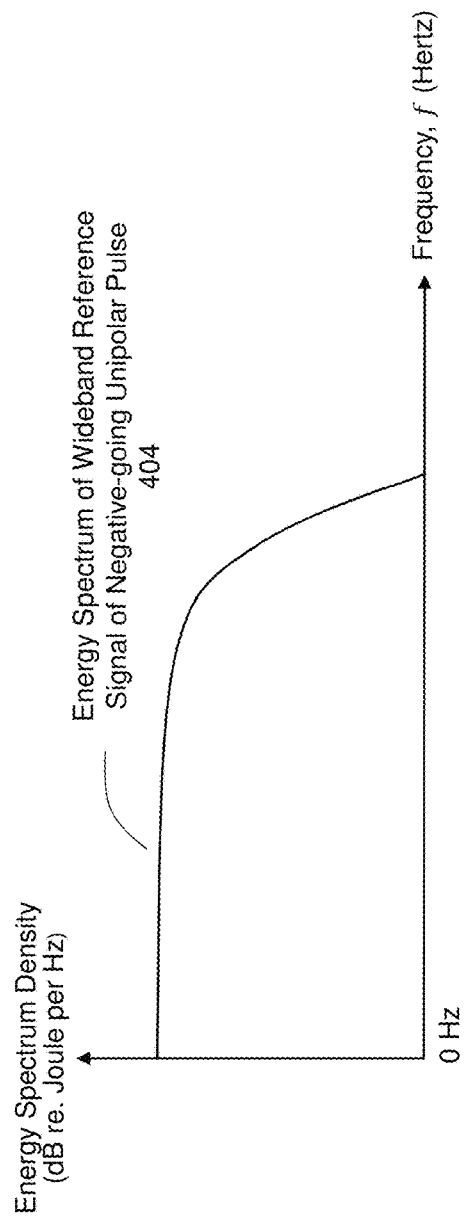

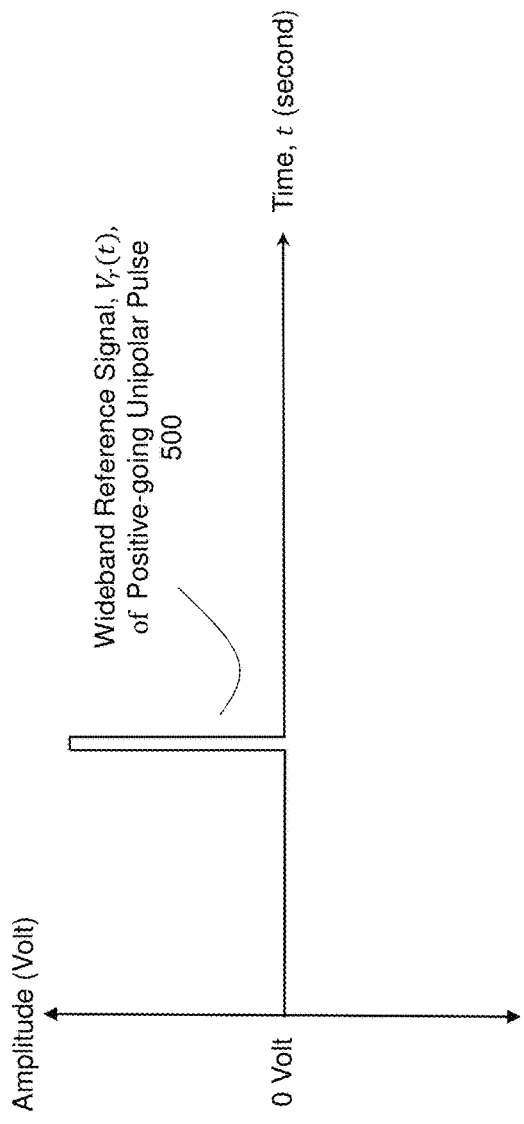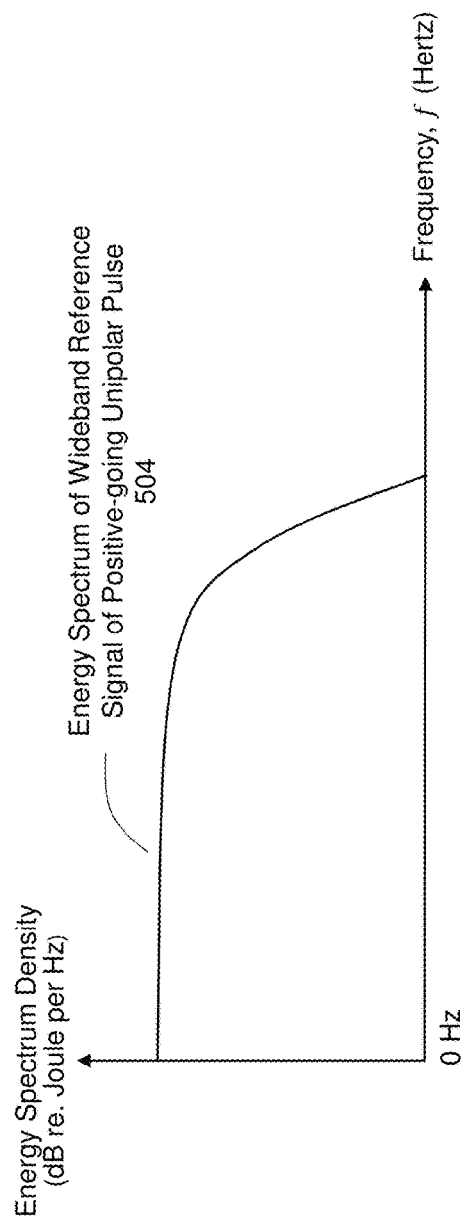

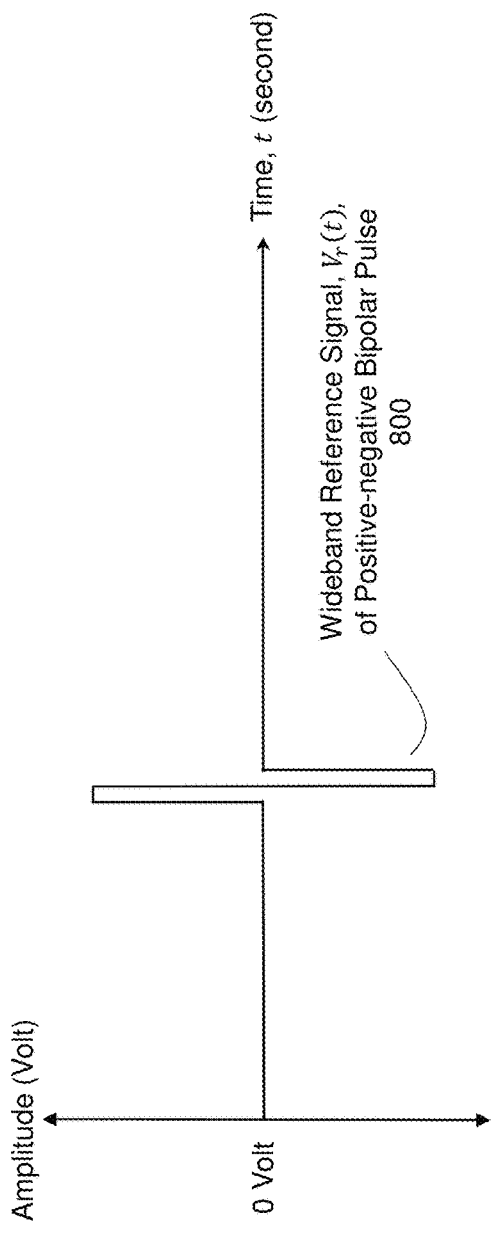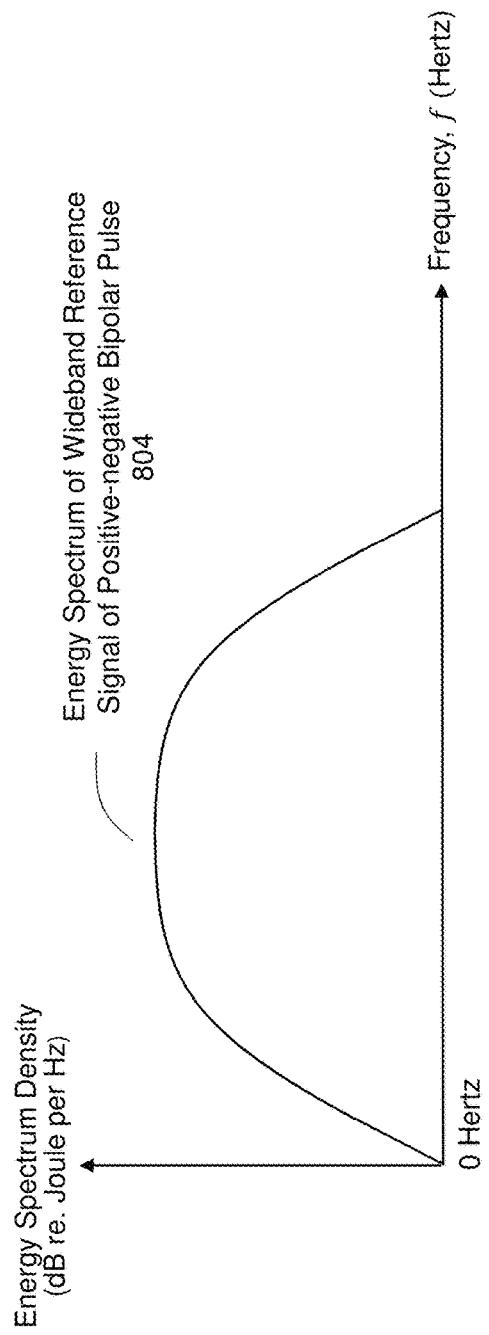

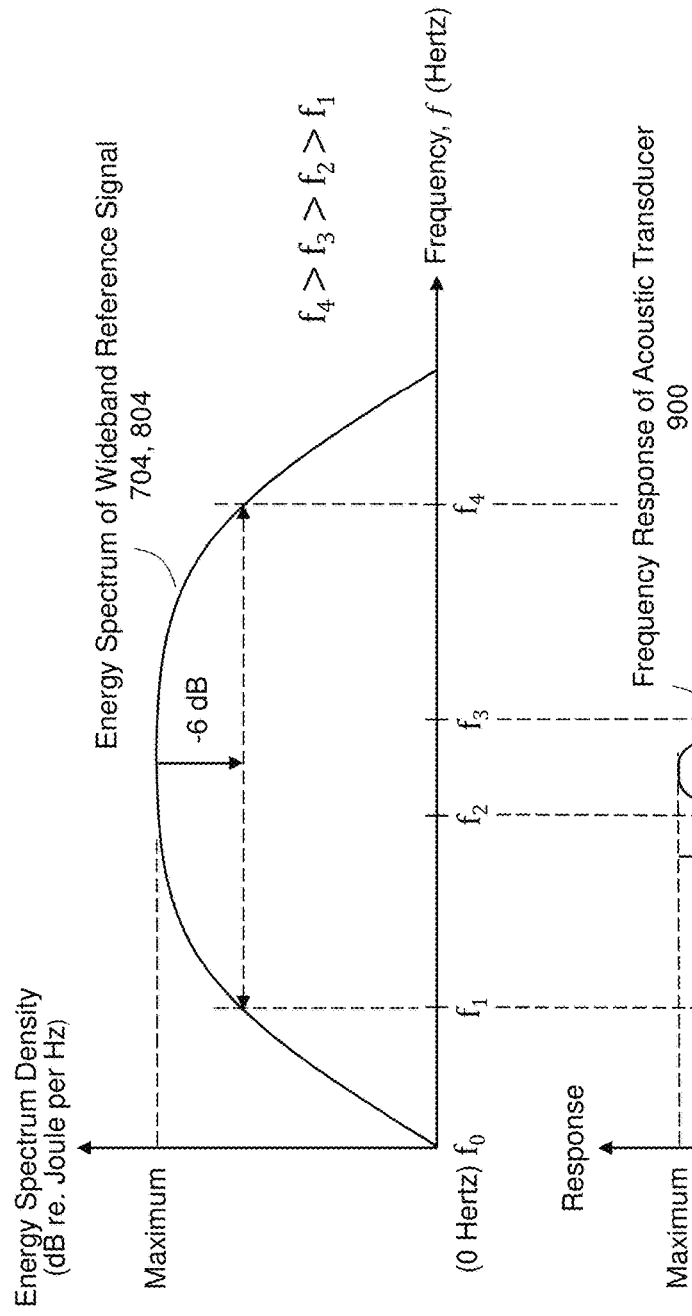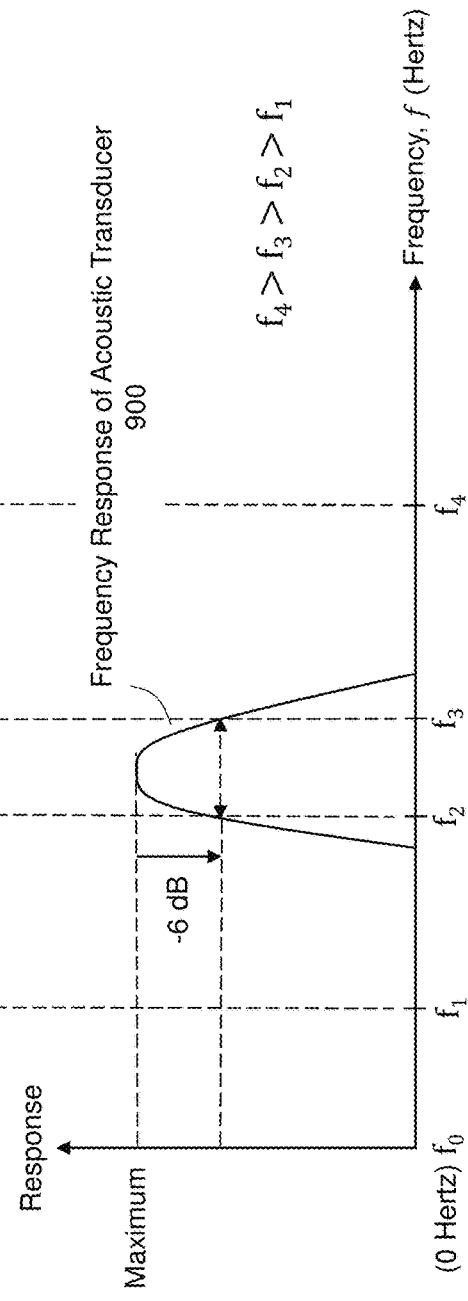

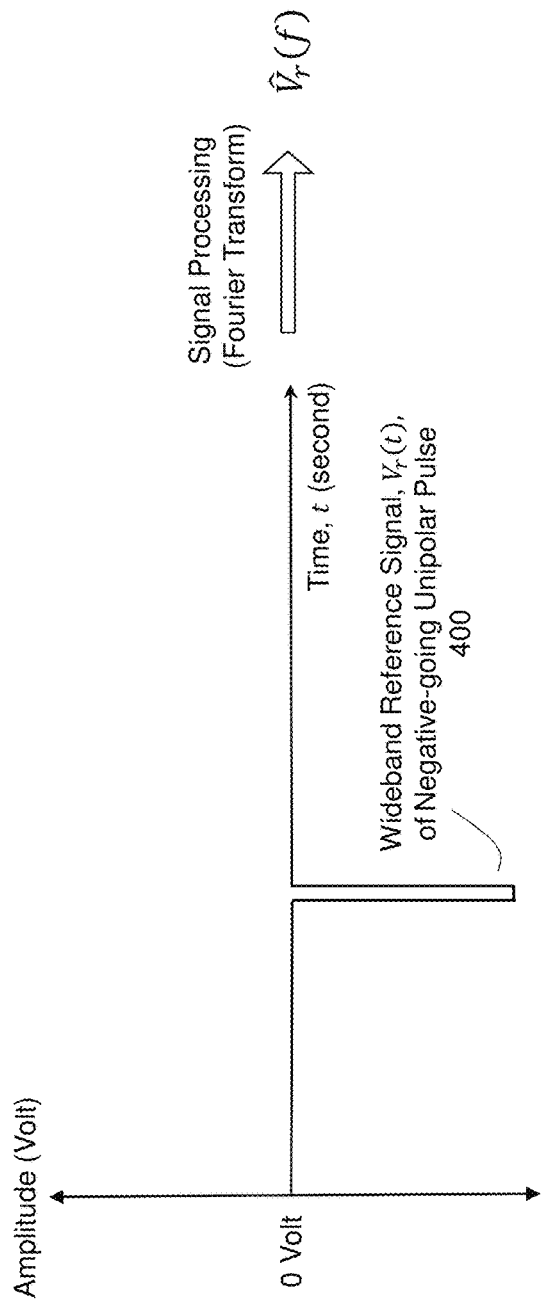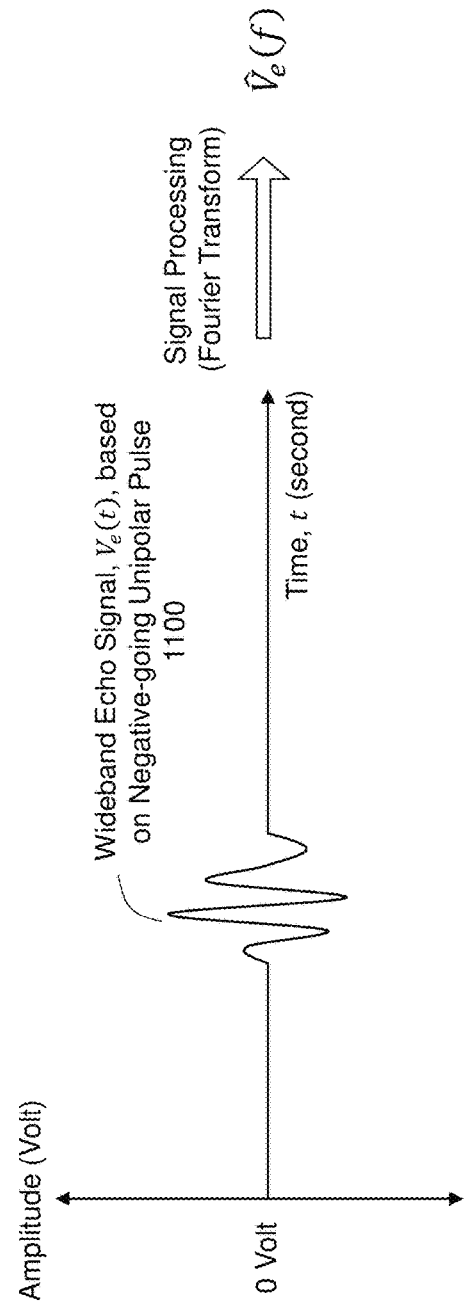

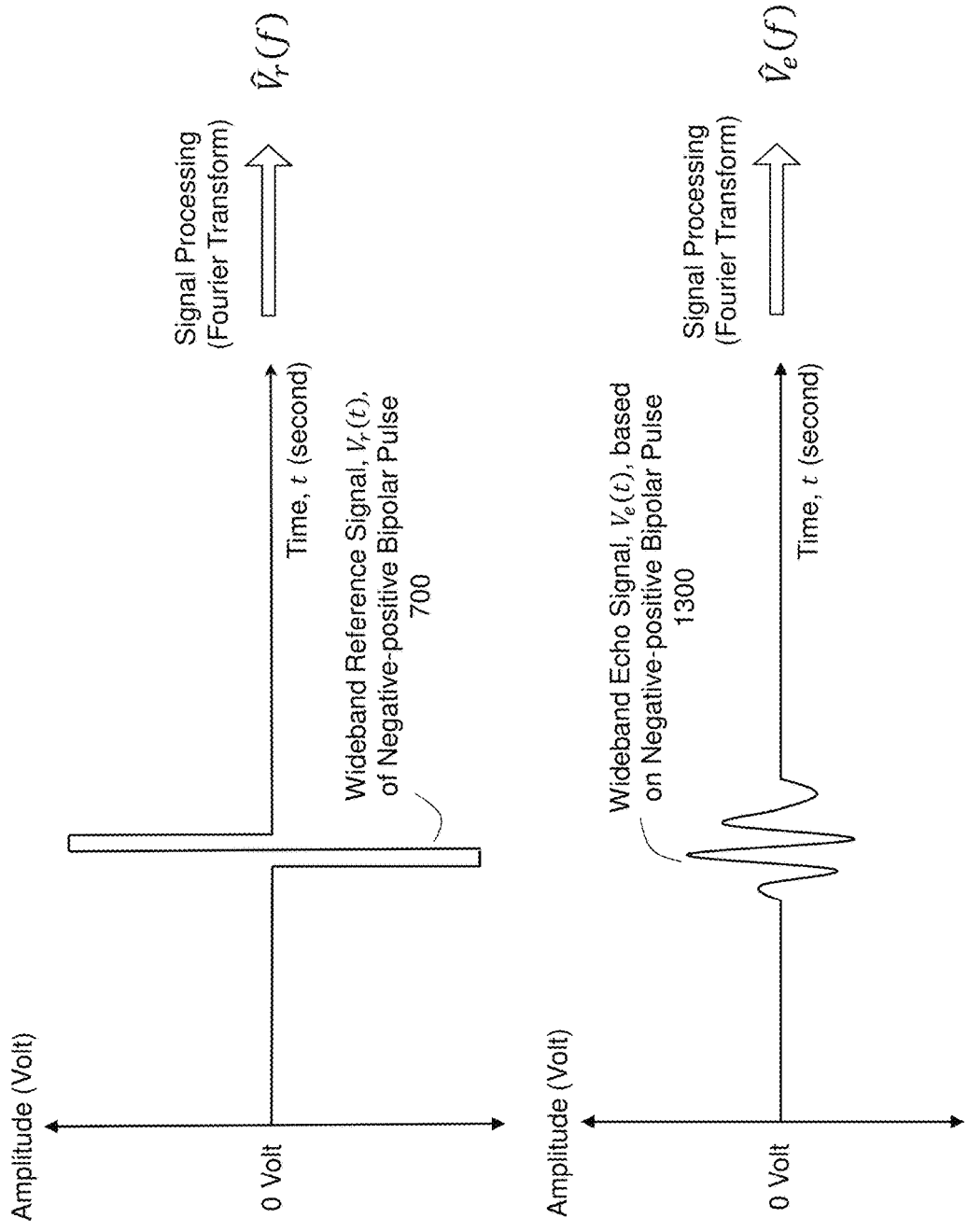

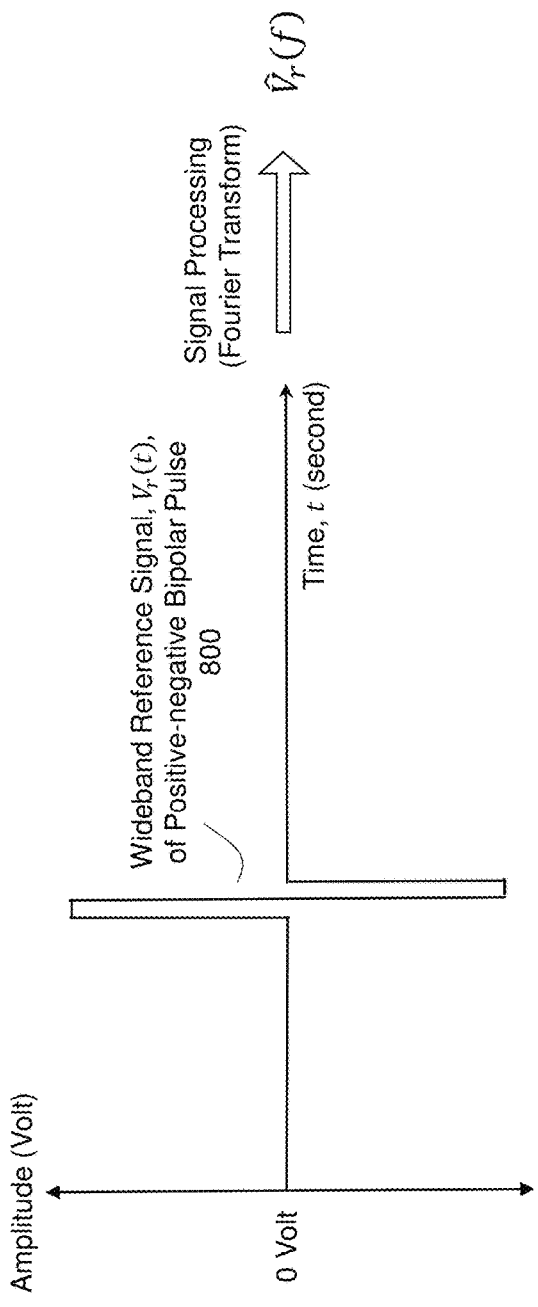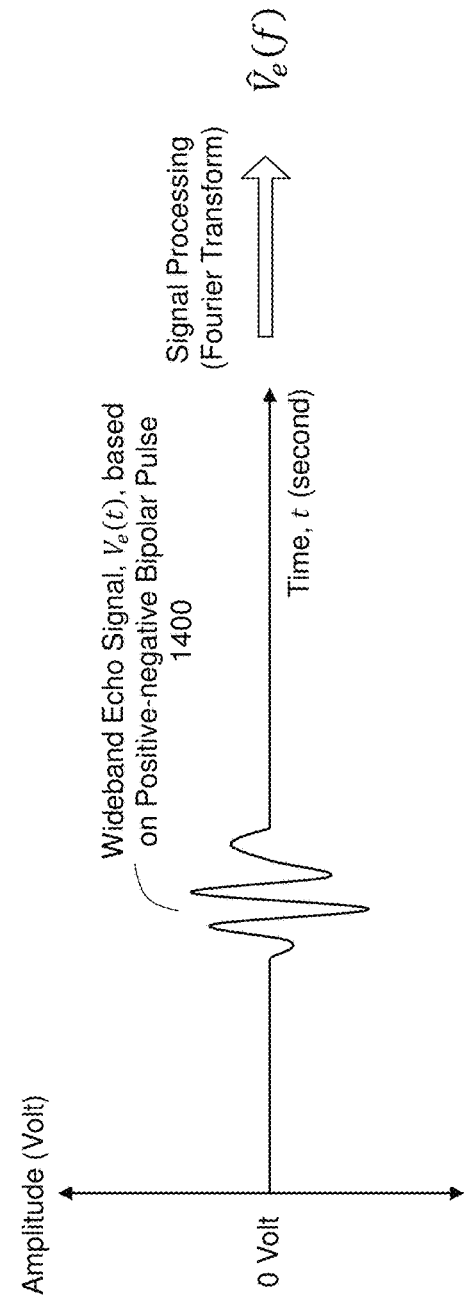

| Frequency (MHz) | 3 | 4 | 5 | 6 | 7 | 8 | 9 | 10 | 11 | 12 | 13 |
|---|---|---|---|---|---|---|---|---|---|---|---|
| Sensitivity (dB) | -71 | -60 | -49 | -47 | -48 | -47 | -48 | -51 | -56 | -66 | -72 |

METHOD AND SYSTEM FOR MEASURING A WIDEBAND LOOP SENSITIVITY FOR AN ACOUSTIC TRANSDUCER

BACKGROUND

Technical Field

The present invention relates to a method and system for measuring a wideband loop sensitivity for an acoustic transducer in an acoustic probe.

Description of Related Art

An acoustic transducer is a key component in an acoustic imaging system. The technologies of acoustic imaging have been frequently employed to non-destructive testing, clinical diagnosis, and under water applications due to such advantages of acoustic imaging as non-invasive, non-ionization, real-time imaging, and cost-effectiveness. For example, acoustic imaging for clinical diagnosis, which is used for assessing the soft tissue structure and blood flow, is currently the most used clinical imaging modality after conventional X-ray radiography.

FIGS. 1A~1B show a typical structure for an acoustic probe in a prior art. An acoustic probe 113 has a transducer array 117A which comprises a plurality of acoustic transducer 117. The number of acoustic transducer 117 in the transducer array 117A is greater than or equal to one.

In the prior art, a sensitivity is used to assess the characteristics of an acoustic transducer 117. FIGS. 2A~2B show the method of sensitivity measurement for an acoustic transducer in an acoustic probe in a prior art. FIG. 2A shows a measuring arrangement for reference signal in a prior art. A sine burst generator 200 is arranged to output a sine burst signal at a specific frequency on an external 50-ohm load as a reference signal $V_r(t)$ 204. FIG. 2B shows a measuring arrangement for an acoustic probe 113 in a prior art. The sine burst generator 200 is electrically coupled to an acoustic probe 113 which is immersed in a water bath 208 with an acoustic mirror 212. The acoustic probe 113 is driven by the sine burst generator 200 and transmits an acoustic sine burst wave 214 at the specific frequency. The acoustic probe 113 receives the reflected sine burst wave 218 from the acoustic mirror 212 and outputs an echo signal $V_e(t)$ 224.

FIG. 3A shows a reference signal for an acoustic probe in a prior art. The reference signal $V_r(t)$ 204 is a sine burst signal with a minimum-run of 15 cycles at a specific frequency; and, a peak-to-peak voltage of reference signal ($V_{ppr}$) is obtained. FIG. 3B shows an echo signal for an acoustic probe in a prior art. The echo signal $V_e(t)$ 224 is a sine burst signal at the specific frequency; and a peak-to-peak voltage of echo signal ($V_{ppe}$) is obtained. A loop sensitivity for the acoustic transducer is calculated based upon the peak-to-peak voltage of echo signal ($V_{ppe}$) to the peak-to-peak voltage of reference signal ($V_{ppr}$).

The disadvantage for the prior art is that one specific frequency is adopted for measuring a loop sensitivity of an acoustic transducer 117 in an acoustic probe 113. In an early stage, traditional acoustic probe responds to narrow band frequency only. However, wideband acoustic probe has been developed due to rapid progress in the acoustic technology development in recent years. Therefore, there is a general need for a method and system for measuring wideband characteristics of an acoustic transducer such as normalized loop frequency response $\hat{X}(f)$ and wideband loop sensitivity $S_L(f)$.

SUMMARY

The present invention discloses a method and system for measuring wideband characteristics of an acoustic transducer in an acoustic probe; the wideband characteristics include normalized loop frequency response $\hat{X}(f)$ and wideband loop sensitivity $S_L(f)$.

A method for measuring a wideband loop sensitivity for an acoustic transducer in an acoustic probe is introduced according to the present invention.

A pulse generator of 50-ohm source impedance, which is used to generate unipolar pulse and/or bipolar pulse, electrically couples to an external 50-ohm load to obtain a wideband reference signal $V_r(t)$ on the 50-ohm load and further obtain a function $\hat{V}_r(f)$ that is a Fourier Transform of the wideband reference signal $V_r(t)$.

In a first and a second embodiment, the adopted pulse is a negative-going unipolar pulse and positive-going unipolar pulse, respectively; and in a third and a fourth embodiment, the adopted pulse is a negative-positive bipolar pulse and positive-negative bipolar pulse, respectively.

The pulse generator of 50-ohm source impedance electrically couples to an acoustic probe for measuring the wideband characteristics of an acoustic transducer. The acoustic probe is immersed into a water bath with an acoustic mirror. The acoustic probe is aligned so that the acoustic wave is normally incident to and reflected from the acoustic mirror. An acoustic transducer in the acoustic probe is driven by the pulse generator of 50-ohm source impedance and transmits a wideband acoustic wave toward the acoustic mirror. The transmitted wideband acoustic wave travels and reaches the acoustic mirror and is reflected backward to the acoustic transducer in the water bath. The acoustic transducer receives the reflected wideband acoustic wave and outputs a wideband echo signal $V_e(t)$; and, a function $\hat{V}_e(f)$ that is a Fourier Transform of the wideband echo signal $V_e(t)$ is obtained.

A normalized loop frequency response $\hat{X}(f)$ of the acoustic transducer is defined as the ratio of the function $\hat{V}_e(f)$ to the function $\hat{V}_r(f)$; that is, $$\hat{X}(f) \stackrel{def}{=} \frac{\hat{V}_e(f)}{\hat{V}_r(f)},$$

according to the present invention.

A wideband loop sensitivity $S_L(f)$ for the acoustic transducer is defined as the following:

$$S_L(f) \stackrel{def}{=} 10 \log|\hat{X}(f)|^2,$$

according to the present invention.

Furthermore, obtain a plurality of wideband loop sensitivity $S_L(f)$ for each and all acoustic transducers in the acoustic probe by performing the measuring step for calculating the wideband loop sensitivity $S_L(f)$ sequentially or randomly over each and all acoustic transducers in the acoustic probe according to the present invention.

The important parameters of an acoustic transducer such as central or resonant frequency, frequency bandwidth, and averaged wideband loop sensitivity can be obtained from the wideband loop sensitivity $S_L(f)$.

The method for measuring the wideband loop sensitivity $S_L(f)$ for an acoustic transducer and method for measuring the plurality of wideband loop sensitivity $S_L(f)$ for each and all acoustic transducers in the acoustic probe are embedded in one of the firmware and the program memory; and, all data of measurement are stored in the storage and output to output devices that is electrically coupled to the control unit, according to the present invention.

A system for measuring a wideband loop sensitivity for an acoustic transducer in an acoustic probe is introduced according to the present invention. The system comprises a pulse generator, a signal processing unit, a transducer selector, and a control unit. The control unit further comprises a firmware, a program memory, and a storage.

BRIEF DESCRIPTION OF THE DRAWINGS

FIGS. 1A~1B show a typical structure for an acoustic probe in a prior art.

FIG. 2A shows a measuring arrangement for reference signal in a prior art.

FIG. 2B shows a measuring arrangement for an acoustic probe in a prior art.

FIG. 3A shows a reference signal for an acoustic probe in a prior art.

FIG. 3B shows an echo signal for an acoustic probe in a prior art.

FIGS. 4A~4B show a negative-going unipolar pulse used as a wideband reference signal and its energy spectrum for a first embodiment according to the present invention.

FIGS. 5A~5B show a positive-going unipolar pulse used as a wideband reference signal and its energy spectrum for a second embodiment according to the present invention.

FIGS. 8A~8B show a positive-negative bipolar pulse used as a wideband reference signal and its energy spectrum for a fourth embodiment according to the present invention.

FIG. 9A shows a typical energy spectrum of wideband reference signal based on a bipolar pulse signal for the third and fourth embodiments according to the present invention.

FIG. 9B shows a typical frequency response for an acoustic transducer in the third and fourth embodiments according to the present invention.

FIG. 11A shows an electrical waveform of a wideband reference signal and its Fourier Transform according to the present invention based on a negative-going unipolar pulse for a first embodiment.

FIG. 11B shows an electrical waveform of a wideband echo signal and its Fourier Transform according to the present invention based on the negative-going unipolar pulse for the first embodiment.

FIG. 13A shows an electrical waveform of a wideband reference signal and its Fourier Transform according to the present invention based on a first bipolar pulse for a third embodiment.

FIG. 13B shows an electrical waveform of a wideband echo signal and its Fourier Transform according to the present invention based on the first bipolar pulse for the third embodiment.

FIG. 14A shows an electrical waveform of a wideband reference signal and its Fourier Transform according to the present invention based on a second bipolar pulse for a fourth embodiment.

FIG. 14B shows an electrical waveform of a wideband echo signal and its Fourier Transform according to the present invention based on the second bipolar pulse for the fourth embodiment.

DETAILED DESCRIPTION OF THE INVENTION

Figure 6A:
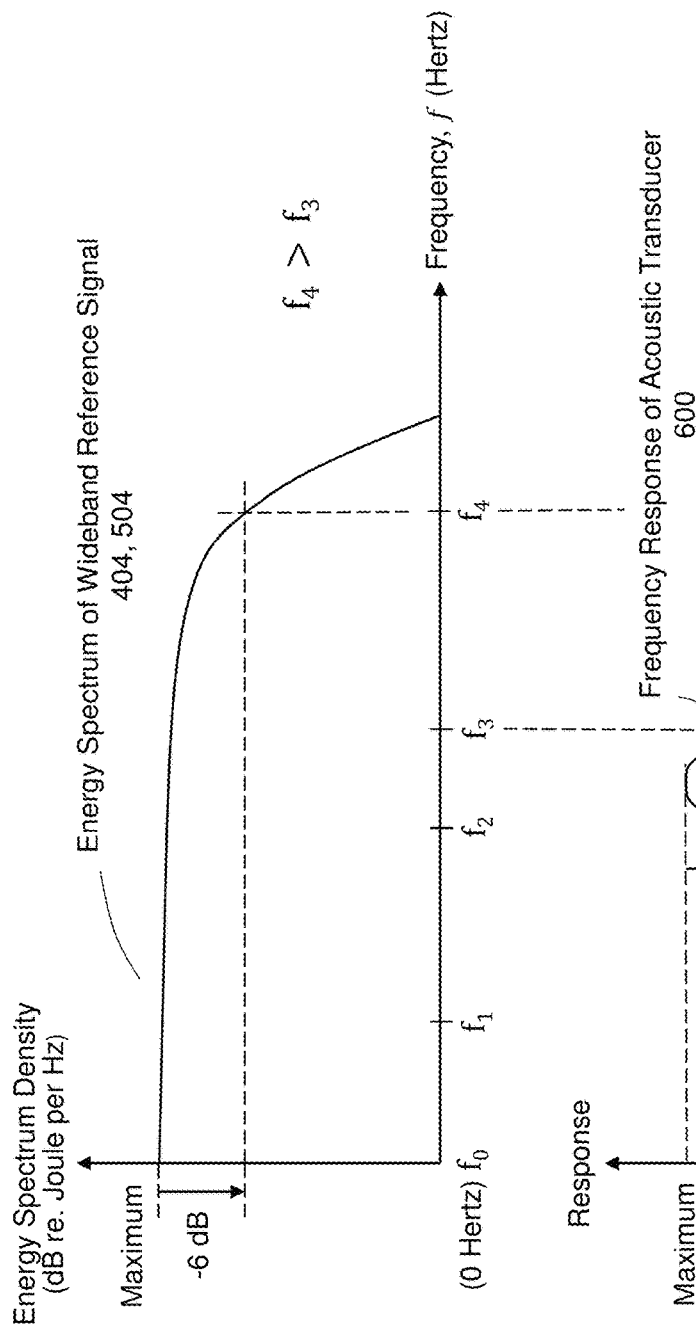
FIG. 6A shows a typical energy spectrum of wideband reference signal based on a unipolar pulse signal for a first and second embodiments according to the present invention.

The present invention discloses a method and system for measuring wideband characteristics of an acoustic transducer in an acoustic probe; the wideband characteristics includes normalized loop frequency response $\hat{X}(f)$ and wideband loop sensitivity $S_L(f)$. The "loop" means the pulse-echo mode in which an acoustic transducer transmits an acoustic wave out and a corresponding reflected echo wave is received by the same acoustic transducer.

A method for measuring a wideband loop sensitivity for an acoustic transducer in an acoustic probe is introduced according to the present invention.

A pulse signal is adopted as a wideband reference signal $V_r(t)$ for measuring wideband characteristics of an acoustic transducer according to the present invention. There are four embodiments of adopted pulse signal used in the present invention, which include a negative-going unipolar pulse 400 for a first embodiment, a positive-going unipolar pulse 500 for a second embodiment, a negative-positive bipolar pulse 700 for a third embodiment, and a positive-negative bipolar pulse 800 for a fourth embodiment, according to the present invention.

FIGS. 4A~4B show a negative-going unipolar pulse used as a wideband reference signal and its energy spectrum for a first embodiment according to the present invention. The wideband reference signal $V_r(t)$ of negative-going unipolar pulse 400 is adopted in the first embodiment, and an energy spectrum of wideband reference signal $\frac{1}{50}|\hat{V}_r(f)|^2$ of negative-going unipolar pulse 404 is obtained, in which the function $\hat{V}_r(f)$ is a Fourier Transform of the wideband reference signal $V_r(t)$ of negative-going unipolar pulse 400.

FIGS. 5A~5B show a positive-going unipolar pulse used as a wideband reference signal and its energy spectrum for a second embodiment according to the present invention. The wideband reference signal $V_r(t)$ of positive-going unipolar pulse 500 is adopted in the second embodiment, and an energy spectrum of wideband reference signal $\frac{1}{50}|\hat{V}_r(f)|^2$ of positive-going unipolar pulse 504 is obtained, in which the function $\hat{V}_r(f)$ is a Fourier Transform of the wideband reference signal $V_r(t)$ of positive-going unipolar pulse 500.

FIG. 6A shows a typical energy spectrum of wideband reference signal based on a unipolar pulse signal for the first and second embodiments according to the present invention. A maximum energy spectrum density of the energy spectrum of wideband reference signal 404, 504 is at 0 Hz ($f_0$). An upper bound frequency ($f_4$) of the energy spectrum of wideband reference signal 404, 504 is a frequency where the energy spectrum density drops down to a certain decibel value (e.g., −6 dB) relative to the maximum energy spectrum density at 0 Hz ($f_0$).

Figure 6B:
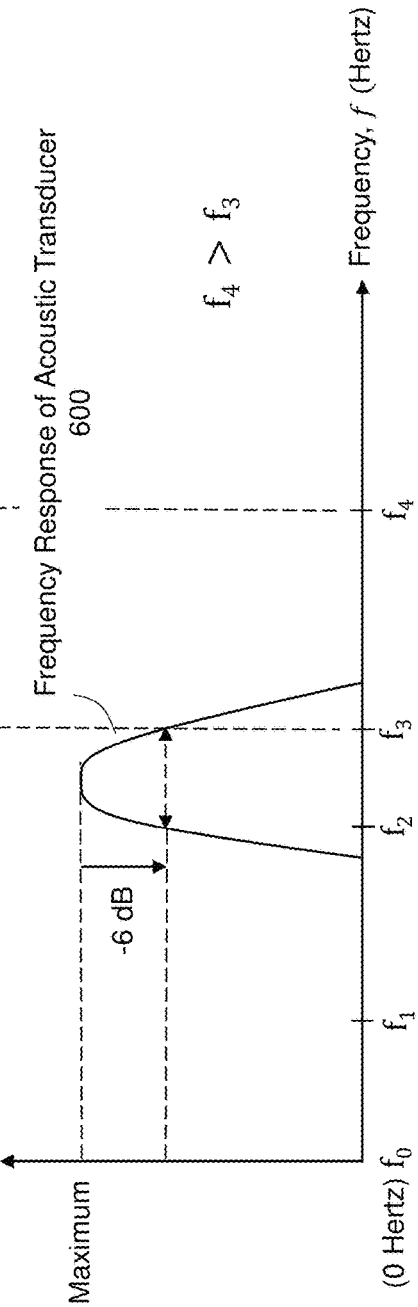
FIG. 6B shows a typical frequency response for an acoustic transducer in the first and second embodiments according to the present invention.

FIG. 6B shows a typical frequency response for an acoustic transducer in the first and second embodiments according to the present invention. A maximum frequency response of an acoustic transducer is usually at its central frequency or resonant frequency. The upper bound frequency ($f_3$) and lower bound frequency ($f_2$) for the frequency response of acoustic transducer 600 are frequencies where the frequency response drops down to a certain decibel value (e.g., −6 dB) relative to its maximum response located at between ($f_2$) and ($f_3$), respectively.

To assure a good signal-to-noise ratio for the measurement in the first and second embodiments, the requirement is that the upper bound frequency ($f_4$) of the energy spectrum of wideband reference signal 404, 504 is greater than the upper bound frequency ($f_3$) of the frequency response of the acoustic transducer 600, that is, $f_4 > f_3$, according to the present invention.

Figure 7A:
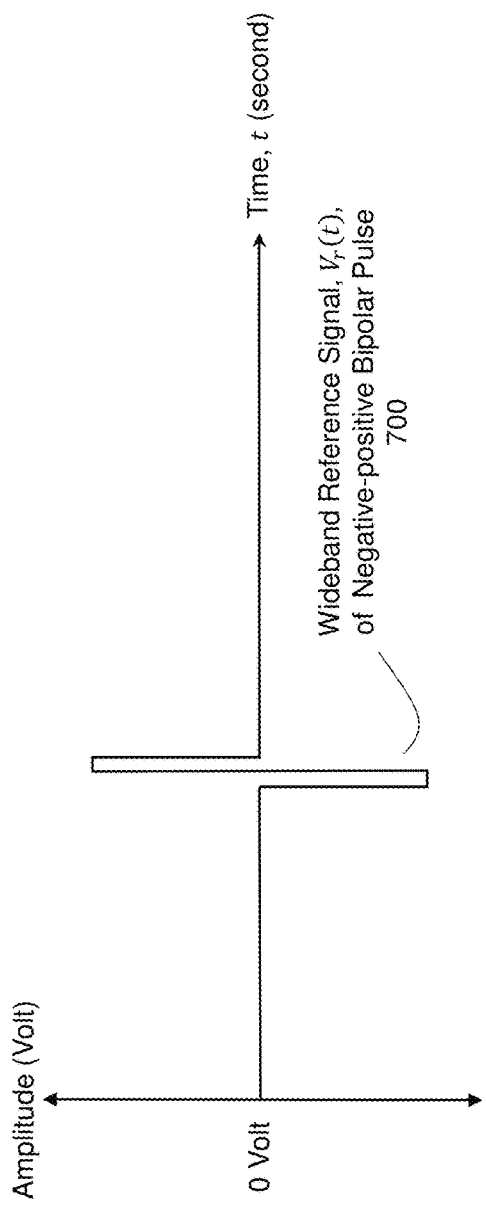
FIGS. 7A~7B show a negative-positive bipolar pulse used as a wideband reference signal and its energy spectrum for a third embodiment according to the present invention.
Figure 7B:
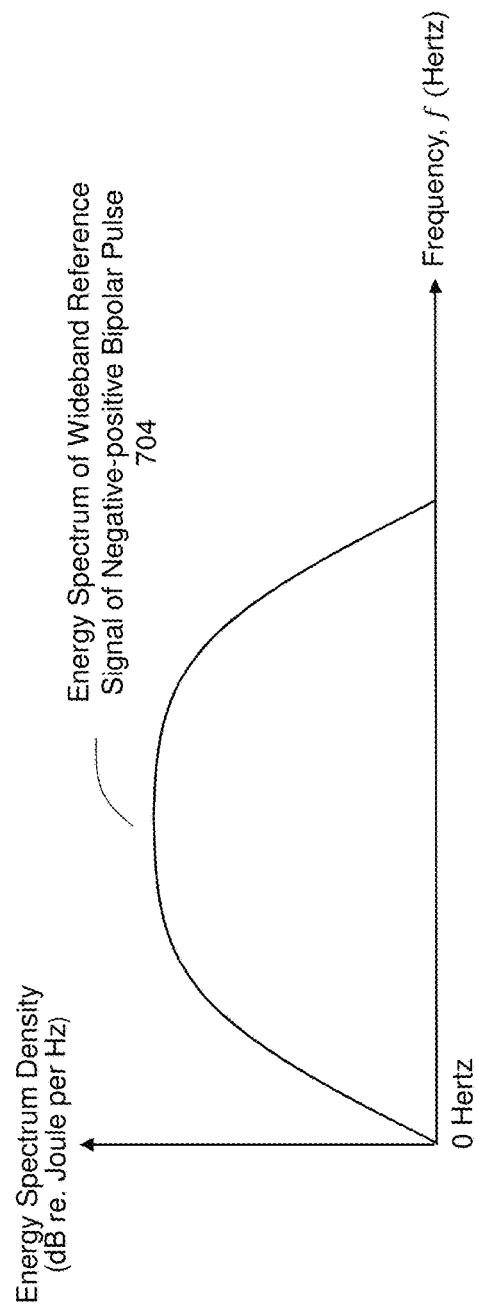

FIGS. 7A~7B show a negative-positive bipolar pulse used as a wideband reference signal and its energy spectrum for a third embodiment according to the present invention. The wideband reference signal $V_r(t)$ of negative-positive bipolar pulse 700 is adopted in the third embodiment, and an energy spectrum of wideband reference signal $\frac{1}{50}|\hat{V}_r(f)|^2$ of negative-positive bipolar pulse 704 is obtained, in which the function $\hat{V}_r(f)$ is a Fourier Transform of the wideband reference signal $V_r(t)$ of negative-positive bipolar pulse 700.

FIGS. 8A~8B show a positive-negative bipolar pulse used as a wideband reference signal and its energy spectrum for a fourth embodiment according to the present invention. The wideband reference signal $V_r(t)$ of positive-negative bipolar pulse 800 is adopted in the fourth embodiment, and an energy spectrum of wideband reference signal $\frac{1}{50}|\hat{V}_r(f)|^2$ of positive-negative bipolar pulse 804 is obtained, in which the function $\hat{V}_r(f)$ is a Fourier Transform of the wideband reference signal $V_r(t)$ of positive-negative bipolar pulse 800.

FIG. 9A shows a typical energy spectrum of wideband reference signal based on a bipolar pulse signal for the third and fourth embodiments according to the present invention. The lower bound frequency ($f_1$) and upper bound frequency ($f_4$) of the energy spectrum of wideband reference signal 704, 804 are frequencies where the energy spectrum density drops down to a certain decibel value (e.g., −6 dB) relative to its maximum located at between ($f_1$) and ($f_4$), respectively.

FIG. 9B shows a typical frequency response for an acoustic transducer in the third and fourth embodiments according to the present invention. A maximum frequency response for the acoustic transducer is usually at its central frequency or resonant frequency. The upper bound frequency ($f_3$) and lower bound frequency ($f_2$) for the frequency response of acoustic transducer 900 are frequencies where the frequency response drops down to a certain decibel value (e.g., −6 dB) relative to its maximum response located at between ($f_2$) and ($f_3$), respectively.

To assure a good signal-to-noise ratio for the measurement in the third and fourth embodiments, the requirement is that the upper bound frequency ($f_4$) of the energy spectrum of wideband reference signal 704, 804 is greater than the upper bound frequency ($f_3$) of the frequency response of the acoustic transducer 900 and the lower bound frequency ($f_1$) of the energy spectrum of wideband reference signal 704, 804 is smaller than the lower bound frequency ($f_2$) of the frequency response of the acoustic transducer 900; that is, $f_4 > f_3 > f_2 > f_1$, according to the present invention.

Figure 10A:
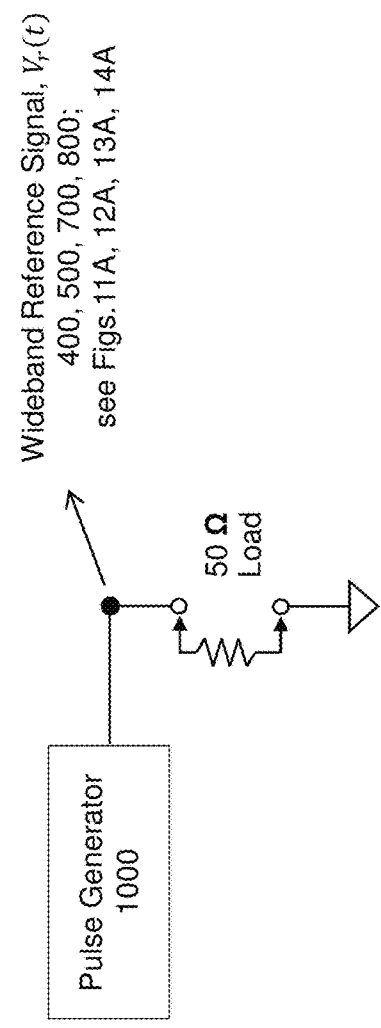
FIG. 10A shows a measuring arrangement for a wideband reference signal according to the present invention.

FIG. 10A shows a measuring arrangement for a wideband reference signal according to the present invention. An external 50-ohm load is electrically coupled to a pulse generator of 50-ohm source impedance 1000 that generates unipolar pulse and/or bipolar pulse to obtain a wideband reference signal $V_r(t)$ 400, 500, 700, 800 on the 50-ohm load.

Figure 10B:
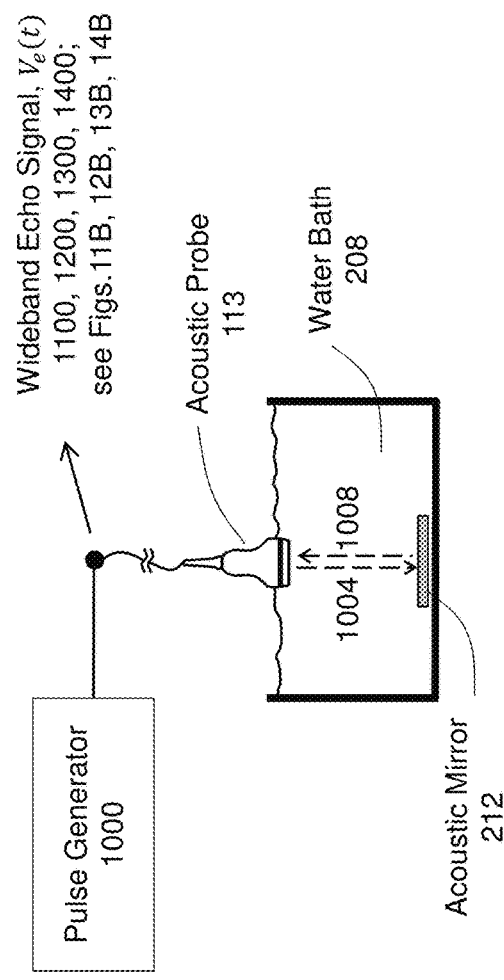
FIG. 10B shows a measuring arrangement for an acoustic probe according to the present invention.

FIG. 10B shows a measuring arrangement for an acoustic probe according to the present invention. The pulse generator of 50-ohm source impedance 1000 electrically couples to an acoustic probe 113 for measuring the wideband characteristics of an acoustic transducer 117. The acoustic probe 113 is immersed into a water bath 208 with an acoustic mirror 212. The acoustic probe 113 is aligned so that the acoustic wave is normally incident to and reflected from the acoustic mirror 212. An acoustic transducer 117 in the acoustic probe 113 is driven by the pulse generator of 50-ohm source impedance 1000 and transmits a wideband acoustic wave toward the acoustic mirror 212. The transmitted wideband acoustic wave 1004 travels and reaches the acoustic mirror 212 in the water bath 208 and is reflected backward to the acoustic transducer 117. The acoustic transducer 117 receives the reflected wideband acoustic wave 1008 and outputs a wideband echo signal $V_e(t)$ 1100, 1200, 1300, 1400 respectively in the four embodiments.

FIG. 11A shows an electrical waveform of a wideband reference signal and its Fourier Transform according to the present invention based on a negative-going unipolar pulse for a first embodiment. The wideband reference signal $V_r(t)$ of negative-going unipolar pulse 400 is adopted in the first embodiment and a function $\hat{V}_r(f)$, that is a Fourier Transform of the wideband reference signal $V_r(t)$ of negative-going unipolar pulse 400, is obtained. Meanwhile, an energy of reference signal ($E_r$) for wideband reference signal $V_r(t)$ of negative-going unipolar pulse 400 is calculated as one of a time-integral of the power of wideband reference signal and a frequency-integral of the energy spectrum density of wideband reference signal; that is, $$E_r = \tfrac{1}{50}\int V_r(t)^2 dt = \tfrac{1}{50}\int |\hat{V}_r(f)|^2 df.$$

FIG. 11B shows an electrical waveform of a wideband echo signal and its Fourier Transform according to the present invention based on the negative-going unipolar pulse for the first embodiment. A wideband echo signal $V_e(t)$ based on negative-going unipolar pulse 1100 is obtained in the first embodiment and a function $\hat{V}_e(f)$, that is a Fourier Transform of the wideband echo signal $V_e(t)$ based on negative-going unipolar pulse 1100, is further obtained. Meanwhile, an energy of echo signal ($E_e$) for wideband echo signal $V_e(t)$ based on negative-going unipolar pulse 1100 is calculated as one of a time-integral of the power of wideband echo signal and a frequency-integral of the energy spectrum density of wideband echo signal; that is, $$E_e = \frac{1}{50} \int V_e(t)^2 dt = \frac{1}{50} \int |\hat{V}_e(f)|^2 df.$$

Figure 12A:
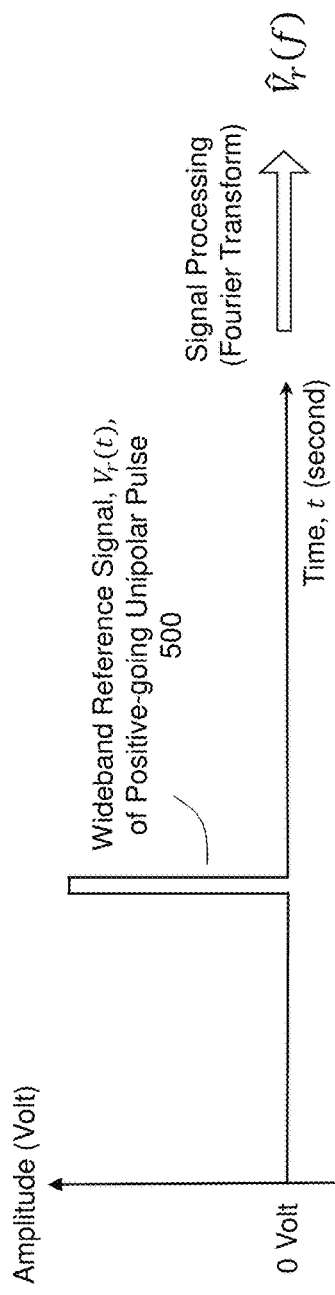
FIG. 12A shows an electrical waveform of a wideband reference signal and its Fourier Transform according to the present invention based on a positive-going unipolar pulse for a second embodiment.

FIG. 12A shows an electrical waveform of a wideband reference signal and its Fourier Transform according to the present invention based on a positive-going unipolar pulse for a second embodiment. The wideband reference signal $V_r(t)$ of positive-going unipolar pulse 500 is adopted in the second embodiment and a function $\hat{V}_r(f)$, that is a Fourier Transform of the wideband reference signal $V_r(t)$ of positive-going unipolar pulse 500, is obtained. Meanwhile, an energy of reference signal ($E_r$) for wideband reference signal $V_r(t)$ of positive-going unipolar pulse 500 is calculated as one of a time-integral of the power of wideband reference signal and a frequency-integral of the energy spectrum density of wideband reference signal; that is, $$E_r = \frac{1}{50} \int V_r(t)^2 dt = \frac{1}{50} \int |\hat{V}_r(f)|^2 df.$$

Figure 12B:
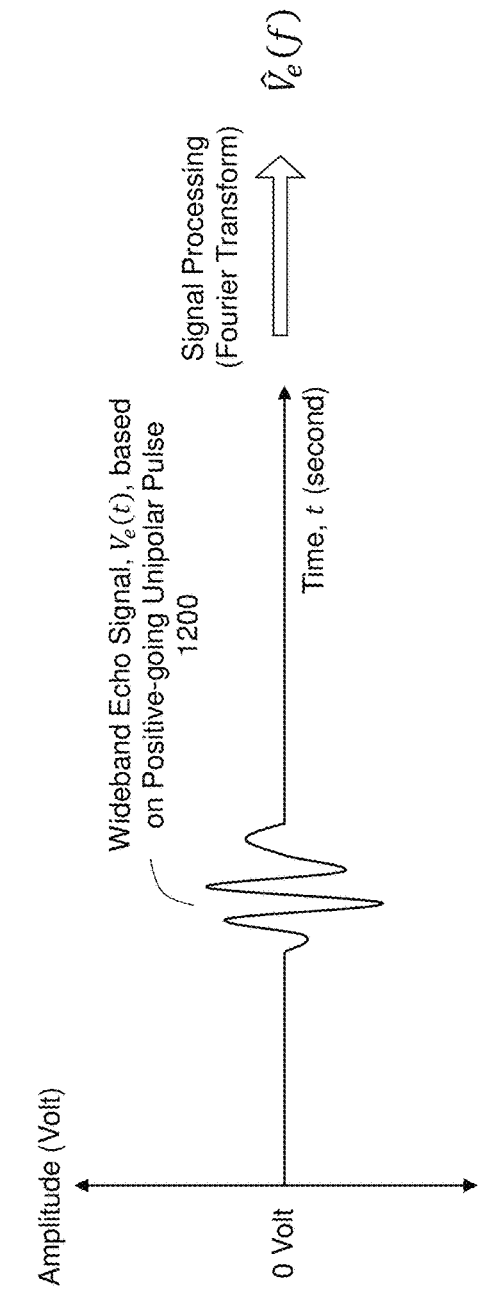
FIG. 12B shows an electrical waveform of a wideband echo signal and its Fourier Transform according to the present invention based on the positive-going unipolar pulse for the second embodiment.

FIG. 12B shows an electrical waveform of a wideband echo signal and its Fourier Transform according to the present invention based on the positive-going unipolar pulse for the second embodiment. A wideband echo signal $V_e(t)$ based on positive-going unipolar pulse 1200 is obtained in the second embodiment and a function $\hat{V}_e(f)$, that is a Fourier Transform of the wideband echo signal $V_e(t)$ based on positive-going unipolar pulse 1200, is further obtained. Meanwhile, an energy of echo signal ($E_e$) for wideband echo signal $V_e(t)$ based on positive-going unipolar pulse 1200 is calculated as one of a time-integral of the power of wideband echo signal and a frequency-integral of the energy spectrum density of wideband echo signal; that is, $$E_e = \frac{1}{50} \int V_e(t)^2 dt = \frac{1}{50} \int |\hat{V}_e(f)|^2 df.$$

FIG. 13A shows an electrical waveform of a wideband reference signal and its Fourier Transform according to the present invention based on a first bipolar pulse for a third embodiment. The wideband reference signal $V_r(t)$ of negative-positive bipolar pulse 700 is adopted in the third embodiment and a function $\hat{V}_r(f)$, that is a Fourier Transform of the wideband reference signal $V_r(t)$ of negative-positive bipolar pulse 700, is obtained. Meanwhile, an energy of reference signal ($E_r$) for wideband reference signal $V_r(t)$ of negative-positive bipolar pulse 700 is calculated as one of a time-integral of the power of wideband reference signal and a frequency-integral of the energy spectrum density of wideband reference signal; that is, $$E_r = \frac{1}{50} \int V_r(t)^2 dt = \frac{1}{50} \int |\hat{V}_r(f)|^2 df.$$

FIG. 13B shows an electrical waveform of a wideband echo signal and its Fourier Transform according to the present invention based on the first bipolar pulse for the third embodiment. A wideband echo signal $V_e(t)$ based on negative-positive bipolar pulse 1300 is obtained in the third embodiment and a function $\hat{V}_e(f)$, that is a Fourier Transform of the wideband echo signal $V_e(t)$ based on negative-positive bipolar pulse 1300, is further obtained. Meanwhile, an energy of echo signal ($E_e$) for wideband echo signal $V_e(t)$ based on negative-positive bipolar pulse 1300 is calculated as one of a time-integral of the power of wideband echo signal and a frequency-integral of the energy spectrum density of wideband echo signal; that is, $$E_e = \frac{1}{50} \int V_e(t)^2 dt = \frac{1}{50} \int |\hat{V}_e(f)|^2 df.$$

FIG. 14A shows an electrical waveform of a wideband reference signal and its Fourier Transform according to the present invention based on a second bipolar pulse for a fourth embodiment. The wideband reference signal $V_r(t)$ of positive-negative bipolar pulse 800 is adopted in the fourth embodiment and a function $\hat{V}_r(f)$, that is a Fourier Transform of the wideband reference signal $V_r(t)$ of positive-negative bipolar pulse 800, is obtained. Meanwhile, an energy of reference signal ($E_r$) for wideband reference signal $V_r(t)$ of positive-negative bipolar pulse 800 is calculated as one of a time-integral of the power of wideband reference signal and a frequency-integral of the energy spectrum density of wideband reference signal; that is, $$E_r = \frac{1}{50} \int V_r(t)^2 dt = \frac{1}{50} \int |\hat{V}_r(f)|^2 df.$$

FIG. 14B shows an electrical waveform of a wideband echo signal and its Fourier Transform according to the present invention based on the second bipolar pulse for the fourth embodiment. A wideband echo signal $V_e(t)$ based on positive-negative bipolar pulse 1400 is obtained in the fourth embodiment and a function $\hat{V}_e(f)$, that is a Fourier Transform of the wideband echo signal $V_e(t)$ based on positive-negative bipolar pulse 1400, is further obtained. Meanwhile, an energy of echo signal ($E_e$) for wideband echo signal $V_e(t)$ based on positive-negative bipolar pulse 1400 is calculated as one of a time-integral of the power of wideband echo signal and a frequency-integral of the energy spectrum density of wideband echo signal; that is, $$E_e = \frac{1}{50} \int V_e(t)^2 dt = \frac{1}{50} \int |\hat{V}_e(f)|^2 df.$$

A normalized loop frequency response $\hat{X}(f)$ for the acoustic transducer is defined as a ratio of the function $\hat{V}_e(f)$ which is a Fourier Transform of the wideband echo signal $V_e(t)$ to the function $\hat{V}_r(f)$ which is a Fourier Transform of the wideband reference signal $V_r(t)$; that is, $$\hat{X}(f) \stackrel{def}{=} \frac{\hat{V}_e(f)}{\hat{V}_r(f)},$$

according to the present invention.

A wideband loop sensitivity $S_L(f)$ for the acoustic transducer is defined as an absolute square of the normalized loop frequency response $\hat{X}(f)$ in decibel; that is, $S_L(f) \equiv 10 \log|\hat{X}(f)|^2$, according to the present invention.

Figure 15:
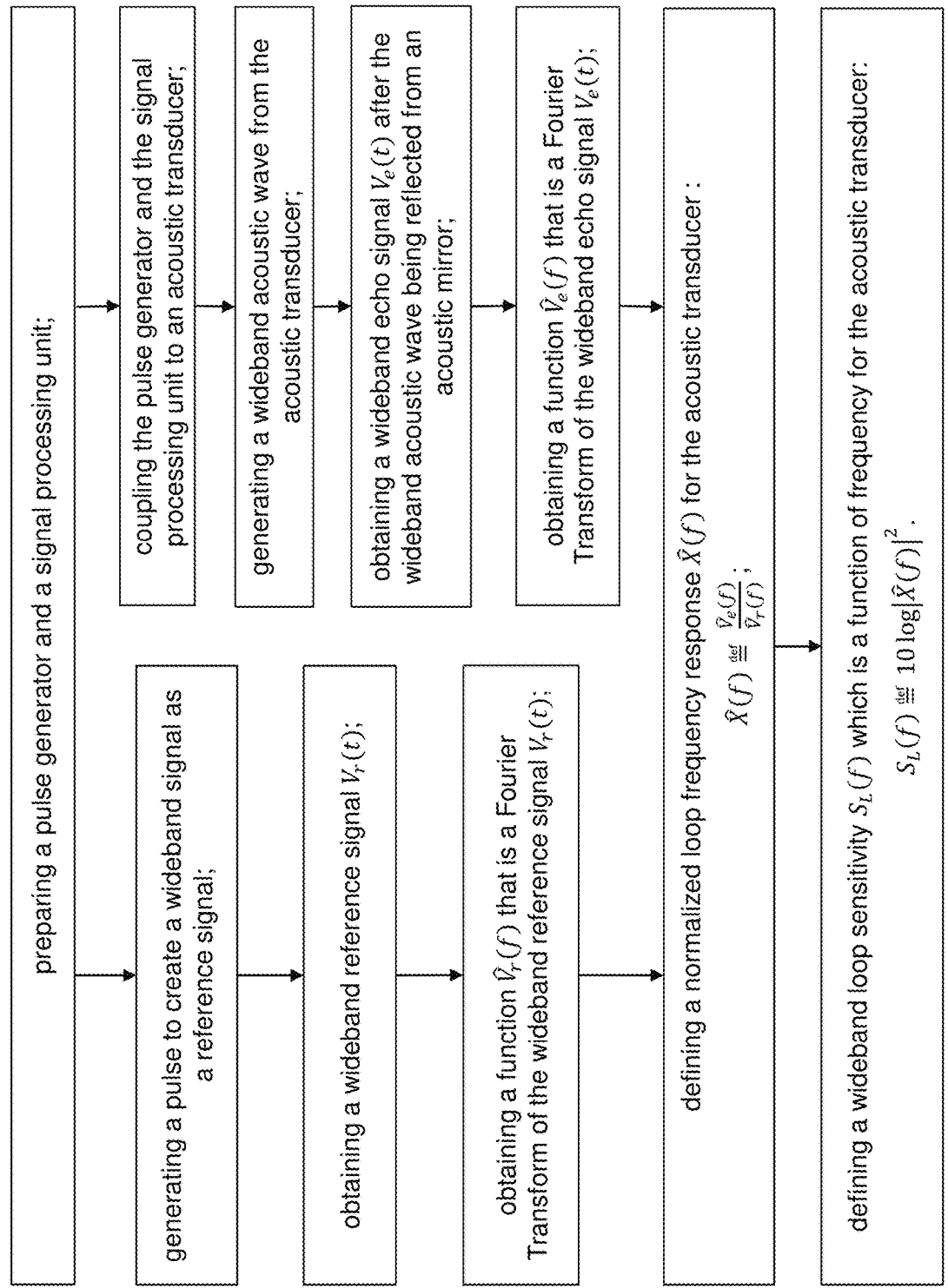
FIG. 15 shows a flow chart for measuring a wideband loop sensitivity of an acoustic transducer according to the present invention.

FIG. 15 shows a flow chart for measuring a wideband loop sensitivity of an acoustic transducer according to the present invention.

The measuring step for obtaining and storing a function $\hat{V}_r(f)$ that is a Fourier Transform of a wideband reference signal $V_r(t)$ comprises:
  preparing a pulse generator and a signal processing unit;
  generating a pulse to create a wideband signal as a reference signal;
  obtaining a wideband reference signal $V_r(t)$;
  obtaining a function $\hat{V}_r(f)$ that is a Fourier Transform of the wideband reference signal $V_r(t)$; and
  storing the function $\hat{V}_r(f)$ that is a Fourier Transform of the wideband reference signal $V_r(t)$ in one of a firmware and a program memory.

The pulse is one of a unipolar pulse and a bipolar pulse. The unipolar pulse is one of a negative-going pulse 400 and a positive-going pulse 500. The bipolar pulse is one of a negative-positive bipolar pulse 700 and a positive-negative bipolar pulse 800.

The measuring step for obtaining and storing a function $\hat{V}_e(f)$ that is a Fourier Transform of a wideband echo signal $V_e(t)$ comprises:

coupling the pulse generator and the signal processing unit to an acoustic transducer;
generating a wideband acoustic wave from the acoustic transducer;
obtaining a wideband echo signal $V_e(t)$ after the acoustic wave being reflected from an acoustic mirror;
obtaining a function $\hat{V}_e(f)$ that is a Fourier Transform of the wideband echo signal $V_e(t)$; and
storing the function $\hat{V}_e(f)$ in a program memory.

The measuring step for defining a normalized loop frequency response $\hat{X}(f)$ for the acoustic transducer comprises:
obtaining the function $\hat{V}_r(f)$ that is a Fourier Transform of the wideband reference signal $V_r(t)$;
obtaining the function $\hat{V}_e(f)$ that is a Fourier Transform of the wideband echo signal $V_e(t)$;
defining a normalized loop frequency response $\hat{X}(f)$ as follows:

$$\hat{X}(f) \stackrel{def}{=} \frac{\hat{V}_e(f)}{\hat{V}_r(f)};$$

and
storing the normalized loop frequency response $\hat{X}(f)$ in the program memory.

The measuring step for defining a wideband loop sensitivity $S_L(f)$ for the acoustic transducer comprises:
obtaining the normalized loop frequency response $\hat{X}(f)$;
defining a wideband loop sensitivity $S_L(f)$ which is a function of frequency for the acoustic transducer as follows:

$$S_L(f) \stackrel{def}{=} 10 \log|\hat{X}(f)|^2;$$

storing the wideband loop sensitivity $S_L(f)$ in a storage device; and
outputting data stored in the storage device.

Furthermore, obtain a plurality of wideband loop sensitivity $S_L(f)$ for each and all acoustic transducers in an acoustic transducer array; the measuring step for which comprises:
performing the measuring step for calculating the wideband loop sensitivity $S_L(f)$ sequentially or randomly over each and all acoustic transducers in an acoustic transducer array;
obtaining a plurality of wideband loop sensitivity $S_L(f)$;
storing the plurality of wideband loop sensitivity $S_L(f)$ in the storage device; and
outputting data stored in the storage device.

Figures 16A, 16B:
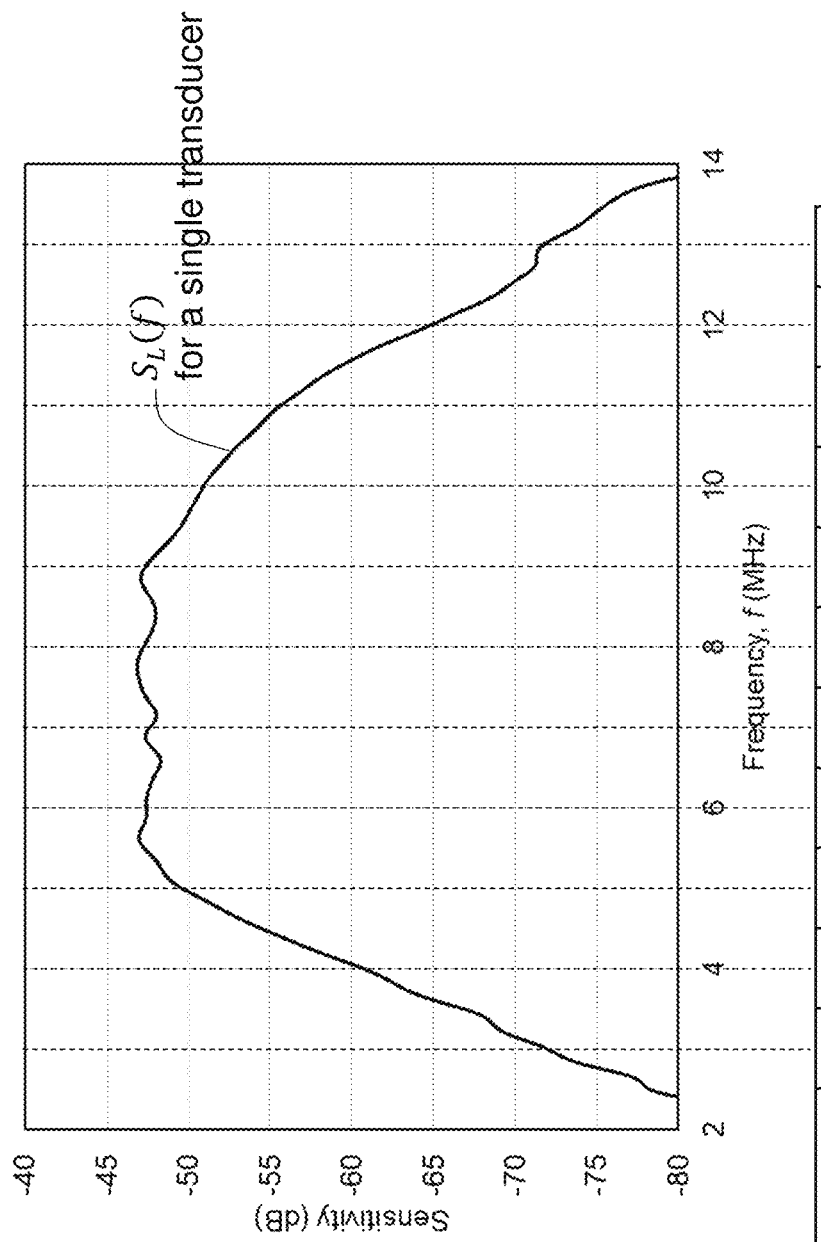
FIG. 16A shows a measured curve of wideband loop sensitivity versus frequency that is obtained in a one-shot measurement for an acoustic transducer according to the present invention.
FIG. 16B shows a table of selected readings from the measured curve of wideband loop sensitivity versus frequency that is obtained in a one-shot measurement for an acoustic transducer according to the present invention.

An example of measuring a wideband loop sensitivity of an acoustic transducer in an acoustic probe was performed according to the present invention and the results are shown in FIGS. 16A~16B. FIG. 16A shows a measured curve of wideband loop sensitivity versus frequency that is obtained in a one-shot measurement for an acoustic transducer according to the present invention. From the measured curve of wideband loop sensitivity versus frequency, some important parameters of the acoustic transducer can be observed; for instance, the central frequency or resonant frequency is at the vicinity of 7.3 MHz, the fractional bandwidth over −6 dB is around 80%, and the averaged wideband loop sensitivity over −6 dB bandwidth is −49.9 dB.

FIG. 16B shows a table of selected readings from the measured curve of wideband loop sensitivity versus frequency that is obtained in a one-shot measurement for an acoustic transducer according to the present invention. The selected readings of loop sensitivity versus frequency include −60 dB at 4 MHz, −47 dB at 6 MHz, −47 dB at 8 MHz, −51 dB at 10 MHz, and −66 dB at 12 MHz etc.

The acoustic transducer under test in the example is in a transducer array of a commercial acoustic probe containing one hundred and ninety-two (192) acoustic transducers. In the measurement, a negative-going unipolar pulse with an amplitude of −75 volts and an upper bound frequency of 55 MHz was adopted as a wideband reference signal. The distance between the acoustic transducer and acoustic mirror is 20 mm. And, the material of the acoustic mirror is stainless-steel with an acoustic reflection coefficient of 0.93 in a water bath.

Figure 17:
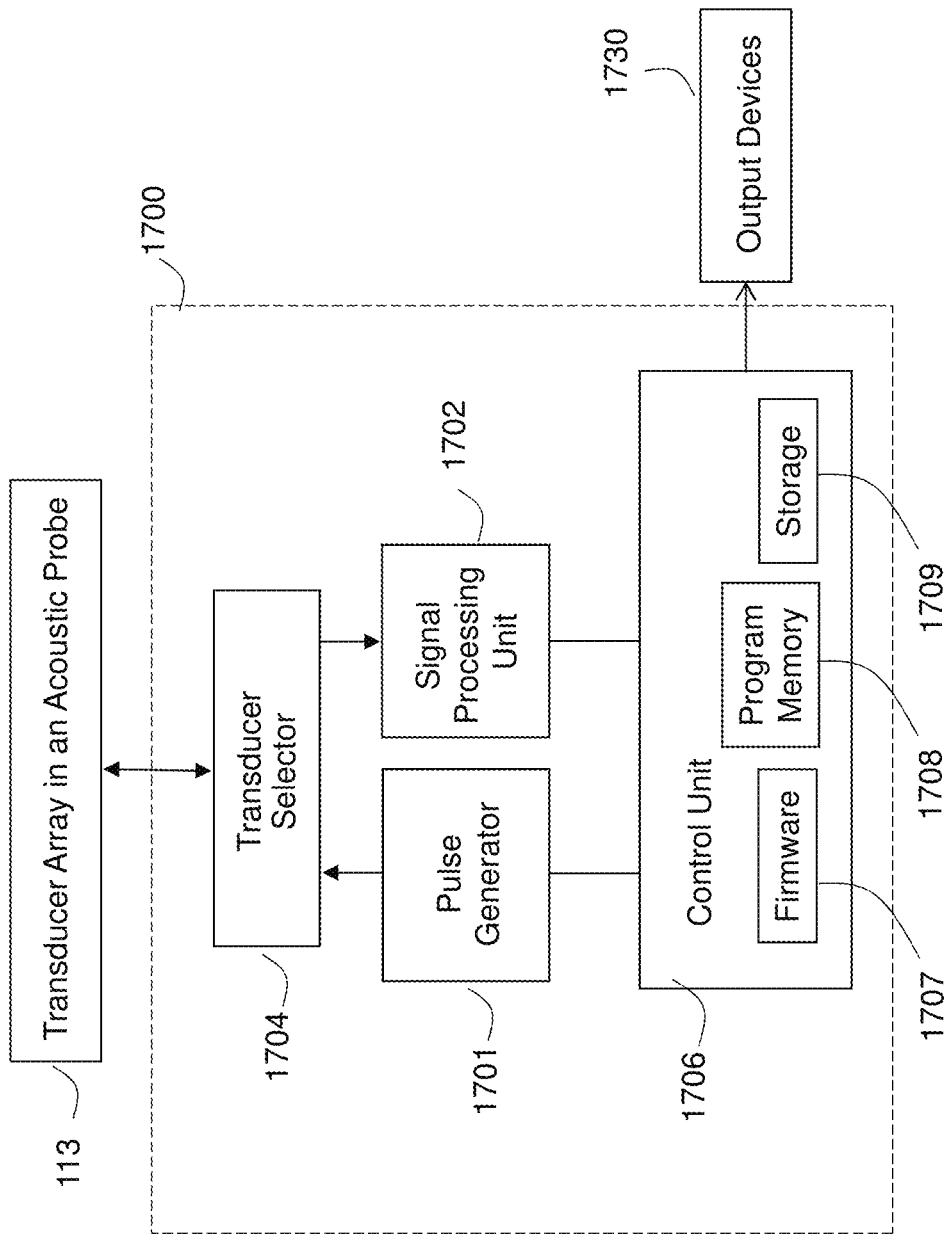
FIG. 17 shows a system for measuring a wideband loop sensitivity of an acoustic transducer in an acoustic probe according to the present invention.

FIG. 17 shows a system for measuring a wideband loop sensitivity for an acoustic transducer in an acoustic probe according to the present invention. The system 1700 comprises a pulse generator 1701, a signal processing unit 1702, a transducer selector 1704, and a control unit 1706. The control unit 1706 further comprises a firmware 1707, a program memory 1708, and a storage 1709.

The control unit 1706 electrically couples to the pulse generator 1701, to the signal processing unit 1702, and to the external output devices 1730.

The pulse generator 1701 is electrically coupled to an acoustic transducer through the transducer selector 1704 for generating a pulse to create a wideband acoustic wave from the acoustic transducer. The pulse is one of a unipolar pulse and a bipolar pulse. The unipolar pulse is one of a negative-going pulse 400 and a positive-going pulse 500. The bipolar pulse is one of a negative-going pulse first and a positive-going pulse second 700 and a positive-going pulse first and a negative-going pulse second 800.

The reflected wideband echo wave is received by the acoustic transducer through the transducer selector 1704 to the signal processing unit 1702 for further processing. The transducer selector 1704 sequentially or randomly selects one transducer of a transducer array in an acoustic probe 113 for measuring.

The measuring method for obtaining a function $\hat{V}_r(f)$ that is a Fourier Transform of a wideband reference signal $V_r(t)$ is embedded in one of the firmware 1707 and the program memory 1708 according to the present invention.

The measuring method for obtaining a function $\hat{V}_e(f)$ that is a Fourier Transform of the wideband echo signal $V_e(t)$ is embedded in one of the firmware 1707 and the program memory 1708 according to the present invention.

The method for measuring a wideband loop sensitivity $S_L(f)$ for the acoustic transducer is embedded in one of the firmware 1707 and the program memory 1708 according to the present invention.

The method for measuring the plurality of wideband loop sensitivity $S_L(f)$ for each and all acoustic transducers in an acoustic transducer array is embedded in one of the firmware 1707 and the program memory 1708 according to the present invention.

All data of measurement are stored in the storage 1709 and can be output to the output devices 1730 according to the present in invention.

The present invention discloses a method and system for measuring wideband characteristics of an acoustic transducer in an acoustic probe; the wideband characteristics includes normalized loop frequency response $\hat{X}(f)$ and wideband loop sensitivity $S_L(f)$. The important parameters of an acoustic transducer such as central frequency or resonant frequency, frequency bandwidth, and averaged wideband loop sensitivity can be obtained from wideband loop sensitivity $S_L(f)$.

While several embodiments have been described by way of example, it will be apparent to those skilled in the art that various modifications may be configured without departing from the spirit of the present invention. Such modifications are all within the scope of the present invention, as defined by the appended claims.

NUMERICAL SYSTEM 113 acoustic probe
117A transducer array
117 acoustic transducer
200 sine burst generator
204 reference signal
208 water bath
212 acoustic mirror
214 transmitted acoustic sine burst wave
218 reflected sine burst wave
224 echo signal
400 wideband reference signal of negative-going unipolar pulse
404 energy spectrum of wideband reference signal of negative-going unipolar pulse
500 wideband reference signal of positive-going unipolar pulse
504 energy spectrum of wideband reference signal of positive-going unipolar pulse
600 frequency response of acoustic transducer
700 wideband reference signal of negative-positive bipolar pulse
704 energy spectrum of wideband reference signal of negative-positive bipolar pulse
800 wideband reference signal of positive-negative bipolar pulse
804 energy spectrum of wideband reference signal of positive-negative bipolar pulse
900 frequency response of acoustic transducer
1000 pulse generator
1004 transmitted wideband acoustic wave
1008 reflected wideband acoustic wave
1100 wideband echo signal based on negative-going unipolar pulse
1200 wideband echo signal based on positive-going unipolar pulse
1300 wideband echo signal based on negative-positive bipolar pulse
1400 wideband echo signal based on positive-negative bipolar pulse
1700 system
1701 pulse generator
1702 signal processing unit
1704 transducer selector
1706 control unit
1707 firmware
1708 program memory
1709 storage
1730 output devices

NOTATION

Reference Signal
($V_{ppr}$) peak-to-peak voltage of reference signal
($E_r$) energy of reference signal; $E_r = \frac{1}{50}\int V_r(t)^2 dt = \frac{1}{50}\int |\hat{V}_r(f)|^2 df$
($BW_r$) bandwidth of reference signal;
($D_r$) energy density of reference signal;

$$D_r = \frac{E_r}{BW_r}$$

$V_r(t)$ wideband reference signal;
$\hat{V}_r(f)$ Fourier Transform of the wideband reference signal $V_R(t)$;
$\frac{1}{50}|\hat{V}_r(f)|^2$ energy spectrum of wideband reference signal;
Echo Signal
($V_{ppe}$) peak-to-peak voltage of echo signal;
($E_e$) energy of echo signal; $E_e = \frac{1}{50}\int V_e(t)^2 dt = \frac{1}{50}\int |\hat{V}_e(f)|^2 df$
($BW_e$) bandwidth of echo signal;
($D_e$) energy density of echo signal;

$$D_e = \frac{E_e}{BW_e}$$

$V_e(t)$ wideband echo signal;
$\hat{V}_e(f)$ Fourier Transform of the wideband echo signal $V_e(t)$;
$\frac{1}{50}|\hat{V}_e(f)|^2$ energy spectrum of wideband echo signal;
Definition
$\hat{X}(f)$ normalized loop frequency response $$\hat{X}(f) \stackrel{def}{=} \frac{\hat{V}_e(f)}{\hat{V}_r(f)}; \hat{X}(f) \stackrel{def}{=} \hat{V}_e(f)/\hat{V}_r(f);$$

X(t) normalized loop time response; Inverse Fourier Transform of the $\hat{X}(f)$
X(t) ≡ Inverse Fourier Transform of the $\hat{X}(f)$
$S_L(f)$ wideband loop sensitivity is defined as an absolute square of the $\hat{X}(f)$ in decibel;
$S_L(f) \equiv 10 \log|\hat{X}(f)|^2$
($S_{LC}$) characteristic loop sensitivity $$S_{LC} \stackrel{def}{=} 10\log\left(\frac{D_e}{D_r}\right)$$

G(t) Inverse Fourier Transform of the $\sqrt{\hat{X}(f)}$;
G(t)=Inverse Fourier Transform of the $\sqrt{\hat{X}(f)}$ self-deconvolution of the X(t); G(t)=Self-deconvolution of the X(t)
B(t) an optimum drive signal on energy efficiency basis for the acoustic transducer;
B(t) ≡ α*G(t), wherein a coefficient α is determined to multiply the function G(t).

What is claimed is:

1. A system for measuring a wideband loop sensitivity for an acoustic transducer among a plurality of acoustic transducers in an acoustic probe, the system comprising:
a pulse generator; and
a control unit electrically coupled to the pulse generator, wherein
the pulse generator is configured to be selectively electrically coupled to a predetermined load for generating, by the pulse generator, a first pulse to create a wideband signal as a reference signal,
the control unit includes a memory storing therein a program or firmware for causing the control unit to obtain a wideband reference signal $V_r(t)$, and
obtain a function $\hat{V}_r(f)$ that is a Fourier Transform of the wideband reference signal $V_r(t)$, and the system further comprises the acoustic probe, and the pulse generator is electrically coupled to the acoustic probe when the predetermined load is not electrically coupled to the pulse generator.

2. The system as claimed in claim 1, wherein the first pulse is one of a unipolar pulse and a bipolar pulse.

3. The system as claimed in claim 2, wherein the unipolar pulse is one of a negative-going pulse and a positive-going pulse.

4. The system as claimed in claim 2, wherein the bipolar pulse is a negative-going pulse first and a positive-going pulse second.

5. The system as claimed in claim 2, wherein the bipolar pulse is a positive-going pulse first and a negative-going pulse second.

6. The system as claimed in claim 1, wherein the control unit is further configured to store the function $\hat{V}_r(f)$ in the memory.

7. The system as claimed in claim 1, wherein
when the pulse generator is electrically coupled to the acoustic probe, the pulse generator is configured to generate a second pulse to create a wideband acoustic wave from a first acoustic transducer among the plurality of acoustic transducers in the acoustic probe, and the control unit is configured to
obtain a wideband echo signal $V_e(t)$ after the wideband acoustic wave being reflected from an acoustic mirror, and
obtain a function $\hat{V}_e(f)$ that is a Fourier Transform of the wideband echo signal $V_e(t)$.

8. The system as claimed in claim 7, wherein
the control unit is configured to
obtain a normalized loop frequency response $\hat{X}(f)$ for the first acoustic transducer as follows:

$$\hat{X}(f) \stackrel{def}{=} \frac{\hat{V}_e(f)}{\hat{V}_r(f)}.$$

9. The system as claimed in claim 8, wherein
the control unit is configured to
obtain a wideband loop sensitivity $S_L(f)$ which is a function of frequency for the first acoustic transducer as follows:

$$S_L(f) \stackrel{def}{=} 10 \log|\hat{X}(f)|^2.$$

10. The system as claimed in claim 9, wherein
the control unit further has a storage device, and is configured to store the wideband loop sensitivity $S_L(f)$ in the storage device.

11. The system as claimed in claim 10, wherein
the control unit is configured to
output the wideband loop sensitivity $S_L(f)$ stored in the storage device.

12. The system as claimed in claim 10, wherein
the control unit is configured to
sequentially or randomly obtain the wideband loop sensitivity $S_L(f)$ for each and all of the plurality of acoustic transducers in the acoustic probe.

13. The system as claimed in claim 12, wherein
the control unit is configured to, after sequentially or randomly obtaining a plurality of wideband loop sensitivity $S_L(f)$ corresponding to the plurality of acoustic transducers in the acoustic probe,
store the plurality of wideband loop sensitivity $S_L(f)$ in the storage device.

14. The system as claimed in claim 13, wherein
the control unit is configured to
output at least one of the plurality of wideband loop sensitivity $S_L(f)$ stored in the storage device.

15. A method for measuring a wideband loop sensitivity for an acoustic transducer among a plurality of acoustic transducers in an acoustic probe, the method using a pulse generator and a control unit electrically coupled to the pulse generator, the control unit including a memory storing therein a program or firmware, the method comprising:
electrically coupling a predetermined load to the pulse generator;
generating, by the pulse generator, a first pulse to create a wideband signal as a reference signal;
obtaining, by the control unit, a wideband reference signal $V_r(t)$;
obtaining, by the control unit, a function $\hat{V}_r(f)$ that is a Fourier Transform of the wideband reference signal $V_r(t)$; and
disconnecting the predetermined load from the pulse generator, and then electrically coupling the acoustic probe to the pulse generator.

16. The method as claimed in claim 15, further comprising:
after said electrically coupling the acoustic probe to the pulse generator,
generating, by the pulse generator, a second pulse to create a wideband acoustic wave from a first acoustic transducer among the plurality of acoustic transducers in the acoustic probe;
obtaining, by the control unit, a wideband echo signal $V_e(t)$ after the wideband acoustic wave being reflected from an acoustic mirror; and
obtaining, by the control unit, a function $\hat{V}_e(f)$ that is a Fourier Transform of the wideband echo signal $V_e(t)$.

17. The method as claimed in claim 16, further comprising:
obtaining, by the control unit, a normalized loop frequency response $\hat{X}(f)$ for the first acoustic transducer as follows:

$$\hat{X}(f) \stackrel{def}{=} \frac{\hat{V}_e(f)}{\hat{V}_r(f)}.$$

18. The method as claimed in claim 17, further comprising:
obtaining, by the control unit, a wideband loop sensitivity $S_L(f)$ which is a function of frequency for the first acoustic transducer as follows:

$$S_L(f) \stackrel{def}{=} 10 \log|\hat{X}(f)|^2.$$

* * * * *